United States Patent [19]
Coll

[11] Patent Number: 5,116,309
[45] Date of Patent: May 26, 1992

[54] URETERAL STENT-CATHETER SYSTEM HAVING VARYING DIAMETER STENT

[76] Inventor: Milton E. Coll, 6 Pear Tree La., Lafayette Hill, Pa. 19444

[21] Appl. No.: 704,718

[22] Filed: May 20, 1991

Related U.S. Application Data

[63] Continuation of Ser. No. 301,090, Jan. 25, 1989, abandoned.

[51] Int. Cl.⁵ .............................................. A61M 37/00
[52] U.S. Cl. ........................................ 604/8; 604/164; 604/281
[58] Field of Search ..................... 604/8–10, 604/93, 95, 170, 280, 281, 264, 282, 283, 49; 128/656–658, 772, 348.1; 606/108

[56] References Cited

U.S. PATENT DOCUMENTS

| | | | |
|---|---|---|---|
| 3,757,768 | 10/1973 | Kline | 604/95 |
| 4,307,723 | 12/1981 | Finney | 604/281 |
| 4,405,314 | 10/1983 | Cope | 604/164 |
| 4,531,933 | 7/1985 | Norton et al. | 604/8 |
| 4,610,657 | 9/1986 | Denson | 604/8 |
| 4,643,720 | 2/1987 | Lanciano | 604/95 |
| 4,671,795 | 6/1987 | Mulchin | 604/8 |
| 4,713,049 | 12/1987 | Carter | 604/8 |
| 4,787,884 | 11/1988 | Goldberg | 128/657 |
| 4,790,809 | 12/1988 | Kuntz | 128/657 |
| 4,790,810 | 12/1988 | Pugh et al. | 604/8 |
| 4,813,925 | 3/1989 | Anderson, Jr. et al. | 604/8 |
| 4,820,262 | 4/1989 | Finney | 604/8 |
| 4,838,879 | 6/1989 | Tanabe et al. | 128/658 |
| 4,913,683 | 4/1990 | Gregory | 604/8 |
| 4,931,037 | 6/1990 | Wetterman | 604/8 |
| 4,957,479 | 10/1990 | Roemer | 604/8 |

FOREIGN PATENT DOCUMENTS 2577804  8/1986  France ...................... 604/8

Primary Examiner—John D. Yasko
Assistant Examiner—Anthony Gutowski

[57] ABSTRACT

A combination ureteral stent-ureteral catheter comprising an elongated flexible tubular member which has proximal and distal ends in the form of curls when present in its internalized stent form and which further comprises an elongated tubular rigid extension attached to the distal end of the stent which allows the combination to function as an externalized ureteral catheter. On extracting the rigid extension from the stent while the device is in place, the distal end of the stent reforms itself into a preformed curl and thereafter functions as a Double J internalized catheter or stent.

9 Claims, 1 Drawing Sheet

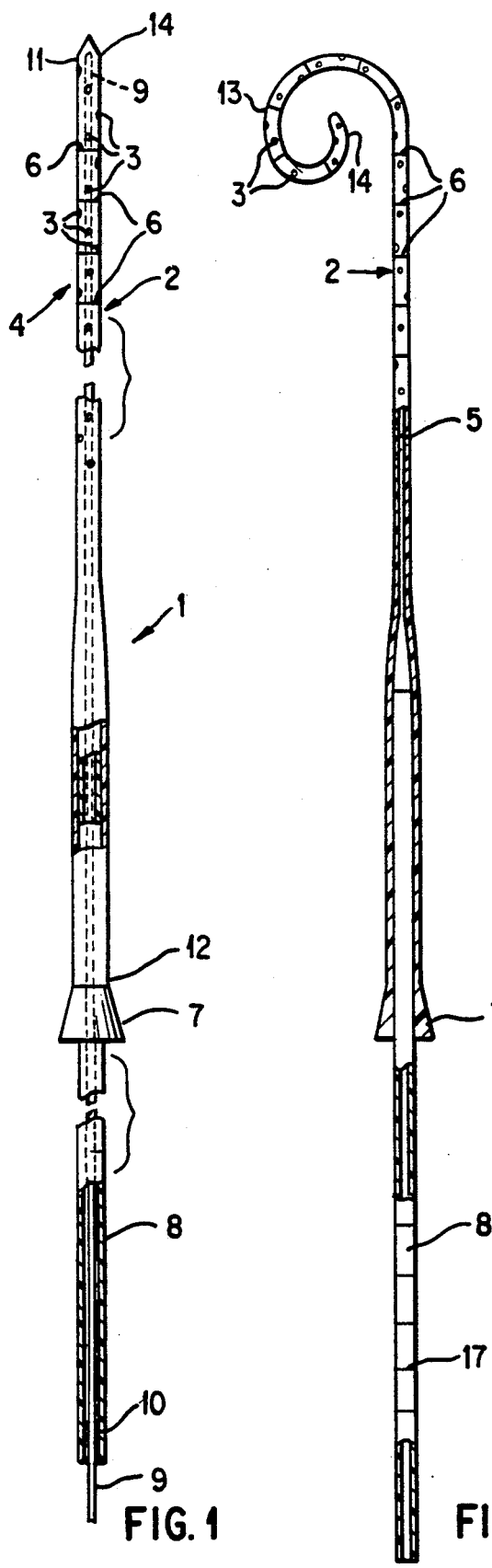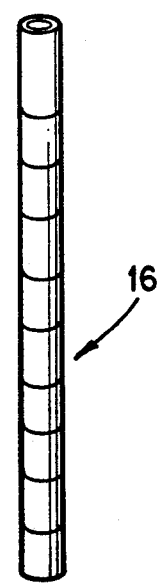
FIG. 1  FIG. 2  FIG. 3  FIG. 4

URETERAL STENT-CATHETER SYSTEM HAVING VARYING DIAMETER STENT

This application is a File-Wrapper-Continuation of application Ser. No. 07/301,090, filed Jan. 25, 1989 (now abandoned).

TECHNICAL FIELD OF THE INVENTION

The present invention relates to a universal catheter inserted by conventional means which, once in place, functions as an external ureteral catheter which can be easily converted into an internalized ureteral catheter or stent.

BACKGROUND OF THE INVENTION

Ureteral catheters and stents are fundamental to the practice of Urology. These devices allow one to bypass and drain an obstructed ureter, determine urine output from a particular renal unit, and inject contrast to study the upper urinary tract. With the advent of newer methods to manage upper urinary tract stones (ESWL and ureteroscopy), the indications and use of ureteral catheters have and will continue to further increase.

The ideal ureteral catheter should allow one to measure urine output from a particular renal unit, drain even tenaciously purulent material, allow injection of contrast for imaging and finally remain indwelling and self contained if longterm ureteral stenting or drainage is required.

The presently available devices consist of external or internal ureteral catheters. Both types are usually passed through the ureteral meatus via a cystoscope, though they can be placed openly through different sites in the urinary tract.

Externalized ureteral catheters drain the upper urinary tract and pass through the bladder, exiting the urethra and draining into an external collecting device. They allow drainage through ports and a central lumen and can be irrigated as needed to drain tenacious and obstructing material. By draining externally, the output from the involved renal unit can be carefully monitored. Contrast can be injected as needed to evaluate the upper tract.

Unfortunately, these devices are not self contained and must be secured to an indwelling urethral catheter or they will migrate and be extruded by ureteral peristalsis. They therefore are not suitable for longterm outpatient care.

With this objective in mind, internalized ureteral catheters were developed. The most commonly used type is a plastic catheter with a curl at both the proximal and distal ends; i.e. Double J catheter. The curls are straightened over a central stiffening wire in order to pass the stent, but are reformed when the stiffening wire is removed. The proximal curl prevents distal migration and thereby keeps the device in the renal pelvis. The distal curl is positioned in the bladder to allow completely internalized drainage. No urethral catheter is needed to secure this type of stent, making it ideal for outpatient management.

U.S. Pat. No. 4,713,049 to Carter; U.S. Pat. No. 4,307,723 to Finney and U.S. Pat No. 4,610,657 to Densaw all show this general approach while U.S. Pat No. 4,531,933 shows a variation of this concept by using helixes to replace hooks.

The devices shown by these patents, however, have disadvantages. The urine output from the involved renal unit can not be recorded as only total urethral urine output can be recorded and this would include both kidneys. Also, since the distal end of the catheter is internalized, it is not possible to irrigate the tube should it become obstructed. Under these circumstances the obstructed catheter could be more detrimental than beneficial as it would occlude an already narrowed ureteral lumen. Since the ureteral catheter can become obstructed without any external indication, the situation can become dramatically acute before it is realized that the internalized stent is no longer serving its purpose. Lastly, as the stent is not externalized, contrast cannot be injected if needed to image the upper tract.

A modification of the usual Double J catheter is available at present that allows injection of contrast via a small lumen in the stiffening wire. This lumen however, is too small to allow reliable and accurate monitoring of urine output or drainage and irrigation of tenacious debris from the involved kidney.

SUMMARY AND OBJECT OF THE INVENTION

It is an object of the present invention to provide a combination catheter-stent that improves on the known prior art devices in that it has the advantages of both an externalized ureteral catheter and the advantage of an internalizable ureteral catheter once the necessity of externalized drainage or access is overcome.

The device of the present invention comprises a Double J catheter with side ports along its proximal half. The proximal end is preferably closed. The distal one-third of the Double J catheter has a wider lumen diameter and is open ended and has consequently a somewhat wider outer diameter than the proximal end. This allows the distal end of the ureteral stent to accept the insertion of a rigid open-ended ureteral catheter. The distal end of the Double-J catheter terminates in a flange of greater outer diameter in order to allow retraction of the stiff ureteral catheter from the stent against an immobilizing abutting device. This rigid ureteral catheter is long enough to exit the urethra and can be drained by an external drainage system.

When the necessity of outside drainage, contrast injection, or monitoring no longer exists, the rigid catheter can be easily disconnected from the flexible ureteral catheter. This allows the part of the stent in the bladder to return to its preformed curl or J shape and then function as a prior art stent of the Double J shape.

DESCRIPTION OF THE DRAWINGS

FIG. 1 is a view of the device as assembled for packaging.

FIG. 2 is a view of the device after insertion and with the stiffening wire removed.

FIG. 3 is a view of the stiff pusher needed for removal of the stiff ureteral catheter.

FIG. 4 is a view of the device in its internalized (stent) form after detachment of the rigid ureteral catheter.

DETAILED DESCRIPTION OF PREFERRED EMBODIMENTS

In a preferred embodiment as shown in the figures the ureteral catheter 1 of the subject invention comprises a flexible plastic tube 2 having apertures 3 along the proximal end 4. The apertures extend between the outside of the catheter and the lumen 5. The catheter 1 may be constructed from any plastic material, preferably a soft flexible material provided with conventional indicating means 6 and is more preferably formed from a radiopaque silicone or silastic material of the type conventionally used for ureteral catheters or stents. The catheter should be marked with conventional centimeter markings to indicate the catheter's position.

Only the proximal tip 14 of the ureteral catheter need be made of radiopaque material but it is preferable that the entire ureteral catheter including the flange be of radiopaque material to facilitate placement of the device.

The distal one third 12 of the flexible plastic tube has an inside and outside diameter wider than that of the proximal end and has a flange 7 that begins about 1 centimeter proximal to the distal end. The distal end of the tube is open. A rigid open ended catheter 8 of the same diameters as the proximal end of the flexible tube is fitted through the flanged end and into the distal end of the flexible plastic tube. The rigid catheter is inserted far enough into the flexible tube to assure secure engagement of the flexible tube. The rigid catheter is held in place by reason of its close fit with the flexible tube. The flange design functions to allow the pusher 16 to disengage the rigid ureteral catheter from the flexible tube by abutting against and immobilizing the flexible tube while the rigid ureteral tube is disengaged. The outside flange diameter is larger than the internal diameter of the pusher. The flange is formed of the same material as the flexible tube.

As shown in FIG. 1 a stiffening wire 9 is used to keep the flexible tube stiff while the catheter as a unit is being inserted. The stiffening wire can be passed through a rubber stopper 10 within the distal end of the rigid catheter. The stopper prevents the wire from receding from the distal end of the ureteral catheter during insertion. When the apparatus has been properly placed, withdrawing the rigid wire will also withdraw the stopper.

Portions adjacent each of the ends 11 and 12 of the flexible tubular member 2 are formed and set in the shape of gentle curls 13 and 14 as shown in FIG. 4. The insertion of the stiff catheter 8 into the flanged end of the flexible stent straightens the curl or J 14 and holds it in straight alignment as shown in FIG. 2.

A stiffening wire 9 straightens the device including the proximal end 11 of the Double J catheter for easy insertion.

A thread or suture 15 can be attached to the distal end of the flexible catheter in order to allow easy removal of the device by pulling on the suture.

The rigid ureteral catheter 8 is formed of material conventionally used for such catheters and is preferably a stiff polymeric material with a hard smooth surface that glides such as polytetrafluoroethylene or nylon.

The rigid ureteral catheter is marked near its distal end. With the rigid ureteral tube inserted in the flexible catheter, the length of rigid tubing between the flange and the marking 17 is equal to the length of the "pusher" 16.

The length of the "pusher" is such that when passed over the rigid ureteral catheter, the flange of the flexible tube will be abutted just as the marking on the rigid ureteral catheter is visualized. This allows the operator to know when the flanged end of the flexible ureteral catheter is immobilized prior to extraction of the rigid ureteral catheter.

The device is sterilely packaged assembled. Different sizes and diameters can be made available with component sizes scaled appropriately. The sizes, lengths and diameters of the various elements are those conventionally used in the art.

As an example of procedure, consider a #7 French Universal Stent. The proximal two thirds of the catheter has a size 7 French and the distal third of the catheter has a size 8.5 French. The distal end of the silastic catheter has a size 9 French flange that begins 1 centimeter proximal to the distal end.

The proximal J is straightened over a 0.038 mm stiff guide wire. This wire also passes through a rigid plastic 7 French ureteral catheter which is inserted into the 8.5 French distal third of the silastic catheter. The wire exits the distal part of the rigid ureteral catheter and is held in place securely by a detachable rubber stopper.

With the wire in place, the proximal end of the J catheter is straightened and can be inserted through a #22 French cystoscope, and passed up in the ureteral orifice to the renal pelvis. The wire then is removed along with the rubber stopper, allowing the proximal curl to form. The rigid ureteral catheter exits through the urethra and the system can be used for an immediate imaging study if needed. To continuously drain the kidney (i.e. to monitor urine output, drain purulent debris, or irrigate to free the system of purulent material) one can secure the rigid ureteral catheter to an indwelling urethral catheter and attach the rigid ureteral catheter to an external drainage bag.

Once the patient is stable and there is no more need for external drainage, the stent can be internalized. The rigid catheter is then completely cleansed with a topical disinfectant and sterile gloves are donned. Packaged separately is a sterile size 8.5 French "pusher" (open ended tube) which then is lubricated and passed over the rigid ureteral catheter until resistance is met as it abuts the flanged distal end of the silastic ureteral catheter. The operator will also know that the flanged distal end of the silastic ureteral catheter has been abutted because the marking on the rigid ureteral catheter will be visualized. Then gently pull the rigid catheter through the pusher, holding the pusher in place. Then gently extract the pusher from the urethra. This will allow the distal end of the silastic catheter to form a curl in the bladder and thereby leave a completely internalized stent. The thread or suture can be left attached to the distal end of the silastic catheter to allow easy extraction through the urethra.

If desired, the stiffening wire can be inserted first using conventional means. After cutting off the proximal tip of the stent, the stent-ureteral catheter device is passed over the wire in order to insert the catheter combination.

Also if desired, various adapters can be secured to the external end of the stiff ureteral catheter in order to permit irrigation, application of contrast solutions to the renal cavity etc.

The thread or suture is preferably of a synthetic polymer with opaque characteristics. It is attached to the stent at any convenient location.

The advantages of the above described device are many. The materials of construction are conventional. The device can be packaged intact and ready to insert. The various elements can be formed in a variety of sizes, lengths and diameters with component sizes scaled appropriately.

The device obviates the need for separate externalized and internalized ureteral catheters. Further, the device is simple in operation and makes use of concepts and designs proven to be effective and reliable.

The device as described in the preferred embodiment specifies insertion of the rigid catheter into the distal third of the flexible tube. However, it is only necessary that the rigid tube be held securely in the stent until it is removed. Further, it can be seen that the specific type of connection described is not critical. Any method of connection that allows the apparatus to function as described is contemplated. Also, as described, the flange, in connection with the stiff pusher, serves only to hold the apparatus in place while the stiff catheter is removed. Any structure that serves to prevent the catheter from being pulled out of the renal cavity when the stiff catheter is removed is contemplated.

It will be readily apparent to those skilled in the art that a number of modifications and changes can be made without departing from the spirit of the invention. Therefore, it is to be understood that the scope of the invention is not to be limited by the foregoing description, but only by the claims.

I claim:

1. A ureteral stent-catheter device for implantation in a ureteral meatus, comprising:
   a) an elongated flexible tubular stent having a pair of preformed set curls at both ends and a fluid passage channel extending substantially the entire length of said stent, comprising:
      i) a drain passage segment having a plurality of drain passages connecting the channel extending along the length thereof to the outside of said stent, the channel having a first preset width dimension, one end of said drain passage segment forming a closed end and forming one end of said stent, a portion of said passage segment forming one of said pair of preset curls;
      ii) a ureteral catheter receiving segment being integral and co-extensive with said passage segment, the channel extending along the length of said receiving segment which has a second preset width dimension, said second width dimension and an outer width dimension of said receiving segment being larger than said first width dimension and an outer width dimension of said drain passage segment respectively, said catheter segment and said passage segment being tapered at the area where they are integrated so as to form a continuous, non-abrupt surface, a portion of said catheter segment forming the other preset curl; and
      iii) a flange formed at a free end of said catheter segment, an end of said flange forming an abutment surface; and
   b) a stiff ureteral catheter insertable into said catheter segment, whereby said other curl formed at said catheter segment of said stent is held in a straight alignment by inserting said catheter to said catheter segment, and wherein, on extraction of said catheter from the catheter segment of said stent, said other curl reforms, said other curl serving to prevent migration of the ureteral device, said catheter comprising:
      i) an elongated stiff tube having an outer width dimension which is substantially equal to said second width dimension of said catheter receiving portion; and
      ii) a channel extending through said tube for permitting insertion of a stiffening wire to straighten said curl formed at said drain segment of said stent.

2. A ureteral stent-catheter device according to claim 1, wherein said first width dimension is 7 French, said second width dimension is 8.5 French, said outer width dimension of said catheter is 7 French, allowing insertion of said catheter into said catheter segment.

3. A ureteral stent-catheter device according to claim 2, wherein said drain passage segment forms approximately proximal two thirds of said stent and said catheter receiving segment forms approximately distal one third of said stent, and further comprising a stiffening wire having a diameter of 0.038 millimeters.

4. A method of using a ureteral stent-catheter for implantation in a ureteral meatus, said ureteral stent-catheter comprising an elongated flexible ureteral stent having preformed set curls at both ends and having a fluid passage channel extending substantially the entire length of said flexible stent, and drain passages connecting said channel to the outside of the stent, said stent having a channel width dimension and an outer width dimension, over its distal one third length, larger than a channel width dimension and an outer width dimension, respectively, of an approximate two-third of its proximal end, said stent also having a flange at its distal end;
   a stiff ureteral catheter for inserting into the distal end of said stent to straighten the curl formed in the distal end; and
   a stiffening wire for passing through said stiff catheter and through said stent to straighten the proximal end of said stent,
   said method comprising the steps of:
      a. inserting said catheter into said distal end of said stent to straighten said curl formed in said distal end of said stent;
      b. inserting said stiffening wire initially through said catheter and then completely through said stent via said channel;
      c. inserting the stent-catheter and wire combination through a cystoscope until the proximal end of said stent is within a renal pelvis;
      d. withdrawing said stiffening wire from said stent-catheter combination thereby allowing the preformed curl at said proximal end to reform and thus allowing the device to function as an externalized ureteral catheter;
      d. extracting said catheter, allowing the preformed distal curl of said stent to reform in the bladder, thus converting the externalized ureteral catheter into an internalized ureteral catheter.

5. A method of using a ureteral stent-catheter for implantation in a ureteral meatus according to claim 4, further comprising the step of retracting said catheter from said stent by passing a tube having openings formed on both ends over said catheter until one end of said tube abuts said flange and a marking on said catheter is visualized, and then, while abutting said tube against said flange, said catheter is pulled through said tube and is withdrawn from the urethra.

6. A method of using a ureteral stent-catheter for implantation in a ureteral meatus according to claim 5, wherein the cystoscope is a size of 22 French and said tube is a size of 8.5 French.

7. A method of using a ureteral stent-catheter for implantation in a ureteral meatus according to claim 4, wherein said stent is a size of 7 French in its proximal two thirds and a size of 8.5 French in its distal third, said catheter is a size of 7 French, and said stiffening wire has a diameter of 0.038 mm.

8. A ureteral stent-ureteral catheter device for implantation in a ureteral meatus, comprising in combination, an elongated unitary flexible ureteral stent having preformed set curls at both ends and a stiff ureteral catheter, said ureteral stent having a fluid passage channel extending substantially the entire length of said stent and drain passages connecting the fluid passage channel to the outside of the stent, said stent having an inside and outside diameter over its distal one third length, wider than that of its proximal end, whereby the set curl associated with the distal end of the stent is held in straight alignment with the stiff ureteral catheter inserted therein and wherein, on extraction of the stiff ureteral catheter from the stent, the preformed distal curl reforms, the curls serving to prevent migration of the ureteral device, wherein the elongated flexible tubular stent has an outside diameter of 7 French in its proximal two thirds, an outside diameter of 8.5 French in its distal one third, wherein junction between said distal two third and distal one third being tapered smoothly so that the outside diameter of 7 French tapers into said outside diameter of 8.5 French, and wherein the stiff ureteral catheter has an outside diameter of 7 French allowing insertion of the ureteral catheter into the distal one third of the ureteral stent, and a tapered flange formed at the distal end of the stent.

9. A method for using an ureteral stent-ureteral catheter combination for implantation in a ureteral meatus comprising the steps of:

a. Preparing a combination of ureteral stent-ureteral catheter comprising:

i. an elongated flexible ureteral stent having preformed set curls at both ends and having a lumen and drain passage connecting the lumen to the outside of the stent the stent having an inside and outside diameter over its distal one third length, wider than that of its proximal end, the stent also having a flange at its distal end, wherein the elongated flexible tubular stent has an outside diameter of 7 French in its proximal two thirds, an outside diameter of 8.5 French in its distal one third and a tapered flange formed at the distal end;

ii. a stiff catheter having an outside diameter of 7 French and insertable into the distal one third of the ureteral stent;

iii. a stiffening wire passed through the stiff ureteral catheter, and thence through the stent to hold the proximal end of the stent in straight alignment with the stent-catheter combination;

b. inserting the combination ureteral stent-ureteral catheter through a cystoscope until the proximal end of the ureteral stent is within a renal pelvis;

c. withdrawing the stiffening wire from the combination ureteral-stent-ureteral combination thereby allowing the preformed curl at said proximal end to reform and thus allowing the device to function as an externalized ureteral catheter; and d. extracting the stiff catheter, allowing the preformed distal curl of the stent to reform, thus converging the externalized ureteral catheter into an internalized ureteral catheter.

* * * * *